United States Patent [19]
Horan et al.

[11] Patent Number: 5,389,084
[45] Date of Patent: Feb. 14, 1995

[54] INSTRUMENT TIP PROTECTOR

[75] Inventors: Robert T. Horan, Northridge; Rudy Gaba, Simi Valley, both of Calif.

[73] Assignee: Devon Industries, Inc., Chatsworth, Calif.

[21] Appl. No.: 112,000

[22] Filed: Aug. 25, 1993

[51] Int. Cl.⁶ ............................................. A61M 5/32
[52] U.S. Cl. .................................. 604/192; 604/199; 604/263; 30/151
[58] Field of Search ...................... 604/192, 199, 263; 606/28–30, 167, 170, 174, 181, 182, 205, 206, 210; 30/143, 151

[56] References Cited

U.S. PATENT DOCUMENTS

| | | | |
|---|---|---|---|
| 311,466 | 2/1885 | Brokhalme | 30/151 |
| 3,234,356 | 2/1966 | Babb | 606/30 |
| 3,381,813 | 5/1968 | Coanda et al. | 604/199 |
| 4,867,747 | 9/1989 | Yarger | 604/263 |
| 5,053,018 | 10/1991 | Talonn et al. | 604/263 |
| 5,147,325 | 9/1992 | Mitchell et al. | 604/192 |

FOREIGN PATENT DOCUMENTS 2622515  12/1976  Germany ................. 604/192

OTHER PUBLICATIONS

Scanlan Single-Use Products—Tip-Guard Instrument Protectors catalog page.
Oxboro Medical International Inc.—Vented Instrument Guards catalog page.
Oxboro Medical International Inc.—Omed Instrument Guards catalog page.
Care Products Catalog Page—Tip-Guard Instrument Protectors.
Sontec Instruments—Tip Covers catalog page.

Primary Examiner—C. Fred Rosenbaum
Assistant Examiner—Frank Wilkens, III
Attorney, Agent, or Firm—Lyon & Lyon

[57] ABSTRACT

A surgical instrument tip protector includes a flexible sheath having an open end into which the tip of a surgical instrument may be inserted. The interior surfaces of the sheath include longitudinal channels and ribs to permit the flow of steam or gases over the tip portion of the instrument, for sterilization, while the tip protector is in place. The inner surfaces of the tip protector are in frictional contact with the instrument tip portion, to prevent the tip protector from inadvertently coming off of the instrument tip. The tip protector has a substantially closed cap end including a small aperture.

14 Claims, 1 Drawing Sheet

INSTRUMENT TIP PROTECTOR

BACKGROUND OF THE INVENTION

The present invention relates generally to tip protectors for surgical instruments having sharp edges or points. More specifically, the present invention relates to removable surgical instrument tip protectors which are vented so as to enable the instrument to be sterilized and aerated, while simultaneously preventing the instruments from being damaged and medical personnel from being injured by the instruments.

The safe and effective use and storage of surgical instruments implicates two important considerations. First, surgical instruments must be kept in sterile environments, so as to prevent the instruments from becoming contaminated by foreign substances or organisms such as bacteria which can be dangerous to the patient. Second, since most surgical procedures require an extremely high level of delicacy and precision, those instruments must be kept undamaged. When the instrument has a sharp cutting edge or point, that edge or point must be kept sharp and precise, to insure that the surgery is conducted accurately and safely. The sharpened portions of the instrument must therefore be prevented from accidentally coming into contact with other objects which may damage the edges or points. Even slight damage to a surgical instrument can render the instrument unusable.

These various considerations often compete with each other. Surgical instruments are, by their nature, designed to cut and puncture, and many have very sharp tip portions. However, very sharp instruments can pose a safety hazard to medical personnel who handle and use them. For example, a sharp instrument may inadvertently pierce through a plastic instrument tray holding the instrument. Additionally, those sharp edges and points can cause damage to other medical instruments or equipment, and the tip portions themselves can be easily damaged or dulled by coming into contact with other instruments or objects. Further, if the tip of an instrument cuts through a sterile container in which the instrument is being stored, the instrument is no longer considered sterile, and must be re-sterilized before use.

Accordingly, a need exists for devices which can be removably attached to surgical instruments to protect the sharp tip portions from being damaged, or from damaging other instruments, and also to protect medical personnel handling the instruments from being injured by the sharp tip portions.

Surgical instruments are commonly sterilized by exposing the instruments to steam and/or one or more gases in an autoclave. The autoclave may also vibrate the instruments. During cleaning, handling and sterilization and loading and unloading the autoclave, the sharpened tip or edge portions of the instruments may be dulled or damaged.

Therefore, there is a need for a device which will protect the sharp tip portions of surgical instruments from damage and which may be used inside an instrument tray. In order for such a device to be effectively used in an autoclave, however, it is necessary that the device protect the tip portion from damage while simultaneously permitting gas and/or steam to freely flow over the protected tip portion to allow the tip portion to be easily sterilized and aerated without having to remove the protective device.

SUMMARY AND OBJECTS OF THE INVENTION

It is therefore an object of the present invention to provide a tip protector which will protect the tip portions of surgical instruments while simultaneously permitting the instrument to be sterilized or aerated.

It is a further object of the present invention to provide a surgical instrument tip protector which will protect the tip portions from being damaged or from accidentally causing injury or damage to persons or other objects, while permitting gas and/or steam to freely flow against the protected tip portion without the need for removing the tip protector.

These and other objects of the invention, which will become apparent from the following detailed description, are accomplished by the surgical instrument tip protector of the present invention comprising a flexible sheath having an open end into which the tip of an instrument may be inserted. The sheath is flexibly disposed so that inner surfaces are in frictional contact with the instrument tip portion, and the sheath fits snugly over the tip portion of the instrument. The sheath may be manufactured in a variety of different shapes and dimensions, so as to accommodate different types, shapes and sizes of surgical instruments. Longitudinal channels are preferably provided on the inner surface of the sheath, as well as on a generally closed cap end of the sheath, to permit the flow of steam and gases over the tip portion of the instrument while the sheath is in place.

A more complete understanding of the instrument tip protector according to the present invention, as well as a recognition of additional objects and advantages thereof, may be obtained by those skilled in the art by reference to the detailed description of the exemplary embodiments below, and to the following drawing figures, in which numbers referenced in the textual discussion correspond to like numbers in the drawing figures.

DETAILED DESCRIPTION OF EXEMPLARY EMBODIMENTS

Figure 1:
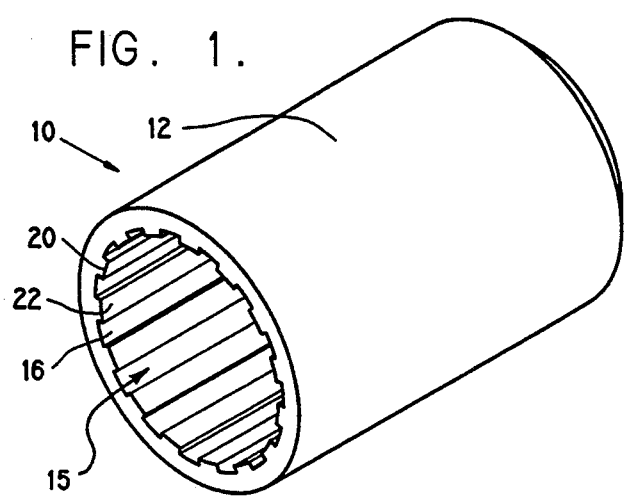
FIG. 1 is a perspective view of the present instrument tip protector.

Referring first to FIG. 1, the present instrument tip protector 10 is generally elongated and tubular in shape, so as to fit for example on a probe or a similar instrument. The tip protector may also be configured in a flat, arcuate design, to accommodate the tip of a scalpel or knife, or in other desired configurations or sizes. It should be understood that the precise dimensions and shape of the tip protector are not crucial, and that the present invention is intended to be applicable to any instrument of the type generally used in surgical procedures. Thus, the present tip protector may have different shapes, sizes, and open end dimensions, to correspond to the dimensions and shape of any such surgical or medical instrument.

As shown in FIG. 1 the present instrument tip protector comprises a sheath 12 having an open end 15, an inner surface designated generally as 16, a generally closed cap end 18, and aperture 14 in the cap end. The inner surface 16 has a plurality of longitudinal channels 20 and ribs 22 preferably parallel to one another. The longitudinal channels 20 are preferably equally spaced apart by the ribs 22. The ribs and channels run in the "longitudinal" direction along the inner surface and terminate adjacent the aperture 14.

In use, the tip portion of a surgical instrument is inserted into the sheath 12 through the open end 15, so that the ribs 22 contact the instrument. A secure fit is created by friction between the ribs and the instrument. The tip protector should be of approximately the size of the tip portion of the instrument on which it is placed. This size selection minimizes the friction forces between the instrument and the tip protector. Thus the instrument can be inserted into and removed from the tip protector preferably with relatively little effort. If the tip protector is too large for the instrument, insufficient friction force will be created and the tip protector may accidentally fall off of the instrument. Conversely, if it is too small, the friction forces exerted by the tip protector against the instrument will be so great that medical personnel may have difficulty attaching and removing the tip protector.

When the instrument has been properly inserted into the tip protector, the ribs are in frictional contact with the instrument. This friction will hold the tip protector in place, covering the sharp tip portion of the instrument. Thus, when the tip protector is in place, it will prevent other objects from coming into contact with these sharpen portions, thereby protecting them from being accidentally damaged.

However, the channels 20, will not contact the instrument. As a result, a space will be created in each channel between the instrument and the sheath 12. The size of this space will be approximately equal to the depth of the longitudinal channels 20, and will exist along the length of the channel. This space will form a tunnel or passage extending longitudinally from the open end 15 and into the sheath along the surface of the instrument. Gas or steam that is directed toward the instrument will be able to enter the tip protector through these tunnels and travel along the tunnel in contact with the instrument, thereby permitting the instrument to be completely sterilized or aerated even with the tip protector securely in place.

It can thus be seen that a tip protector according to the exemplary embodiment of the invention described above provides a convenient and advantageous means for covering and protecting the tip portions of surgical instruments, while at the same time permitting the protected portion to be sterilized and aerated as desired. When the tip protector of the present invention has been placed onto an instrument, the tip protector will prevent persons or other objects from coming into contact with the sharpened tip portions of the instrument. However, the space between the instrument and the sheath that is created in each tunnel will permit gas and steam to freely flow into the sheath and over the surface of the instrument.

In the embodiments described above, the tip protector is generally formed of a material that is sufficiently strong to prevent the sharp tip portion of the instrument on which it is placed from accidentally penetrating or cutting the sheath. A secure fit is created by a slight friction force between the instrument and the ribs.

Alternatively, an even more secure and flexible tip protector may be achieved by forming the sheath from a slightly elastic material which may expand slightly to accommodate the instrument, and, after the instrument is inserted, to slightly contract against the instrument so that the ribs are pressed against the instrument, thereby creating an even greater friction force between the sheath and the instrument, resulting in a more secure fit. However, if an elastic material is used, the material must still be strong enough to prevent the sharpened instrument from accidentally penetrating or cutting the sheath. Further, the tip protector must be sufficiently rigid that, when the sheath has been slightly stretched to fit over an instrument, that stretching does not destroy the integrity of the longitudinal channels.

In addition to achieving a more secure fit, the use of a more flexible material will permit the tip protector to conform to a variety of different medical instruments of approximately similar general size. In a preferred embodiment, the tip protector may be formed of PVC and polyurethane. The Food and Drug Administration has approved PVC and polyurethane for the exemplary surgical purposes hereindescribed. However, the tip protector could also be formed of any material having similar characteristics. It should be understood that the precise material used to form the sheath is not critical to the present invention except as they affect the features and advantages hereindescribed.

Whatever the precise material used, the tip protector should preferably be sufficiently flexible to adapt to different instruments of approximately the same overall size as the opening 15 without excessive stretching of the sheath. For example, a generally tubular tip protector may be adaptable to fit securely on a hook-shaped instrument. Larger or smaller tip protectors may be used to conform to instruments of different dimensions, as appropriate. Therefore, the tip protectors of the present invention are advantageously provided in a variety of different shapes and sizes, in order to fully accommodate the existing range of surgical instruments. The present tip protector may be tubular, as in the figures, or it may be tapered, square, arcuate, tear-drop shaped, etc., as is necessary and appropriate to accommodate the particular surgical instrument for which protection is desired.

Figure 2:
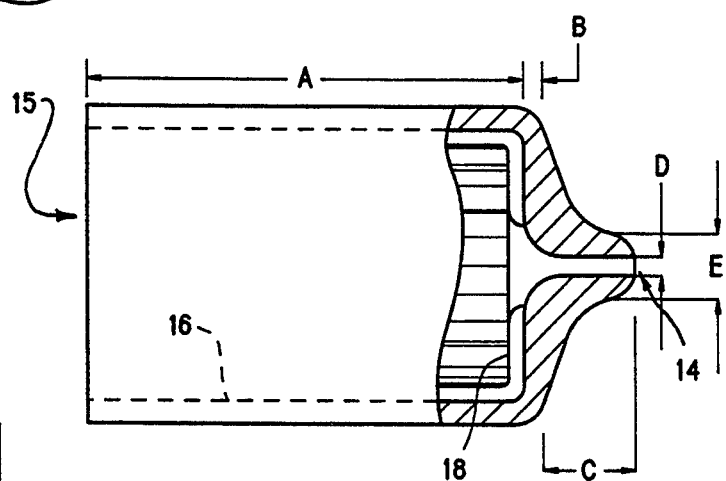
FIG. 2 is a side elevation view thereof in part section.
Figure 3:
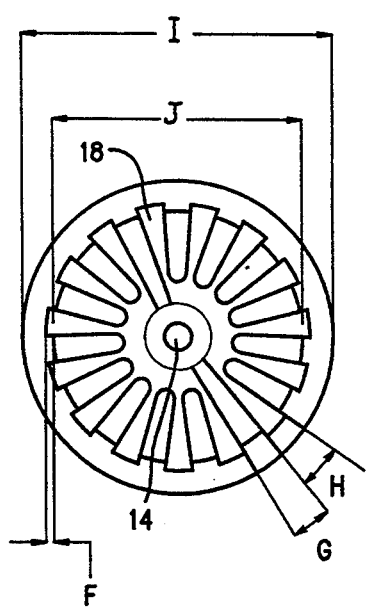
FIG. 3 is an end view looking into the open end of the tip protector.

Referring to FIGS. 2 and 3, in one preferred embodiment the depth A of the inside space of the sheath is preferably 0.75 inch, wall thickness B 0.05 inch and cap height C 0.02 inch. The aperture diameter D is preferably 0.03 inch, cap diameter E 0.13 inch, sheath outside diameter I 0.51 inch, and sheath inside diameter (channel to channel) J 0.41 inch. Rib height F is preferably 0.03, and angles G and H both about 12 degrees.

By slightly modifying the tip protector, other advantages can also be achieved. For example, tip protectors of different colors or having logos or patterns imprinted on the exterior may be used to identify or differentiate the different types of instruments on which they are placed. Alternatively, tip protectors may be made of transparent material, so that the protected instrument can be easily identified, or the tip protectors may be formed of a material that is conducive to being marked by a felt-tip marker or pen.

Further, the tip protector may also be formed of a material that may be cut with a pair of scissors, so that medical personnel can easily adjust the dimensions or length of a tip protector to fit a particular instrument. All of these modifications, and others which are readily apparent to those skilled in the art, should be understood as being fully consistent with and included within the scope of the present invention.

The instrument tip protector of the present invention may be implemented in numerous ways. The particular embodiments discussed hereinabove are intended to illustrate what are believed to be particularly useful specific applications of the present invention, and the disclosed embodiments are not intended to limit the scope of the invention. Any other adaptations, modifications or embodiments incorporating the invention are expressly deemed to be within the scope of the following appended claims.

We claim:

1. A surgical instrument tip protector comprising:
   a substantially solid, elastic sheath having an inner surface and an open end adapted to receive an instrument tip; and
   a plurality of longitudinal ribs disposed on the inner surface of the sheath and adapted to contact the surface of an instrument tip covered by the sheath to provide spaces about the instrument tip through which fluid or gases may flow.

2. A surgical instrument tip protector comprising:
   a substantially solid, flexible sheath having an inner surface and an open end adapted to receive an instrument tip; and
   a plurality of longitudinal ribs disposed on the inner surface of the sheath to provide spaces about an instrument tip covered by the sheath, through which fluid and gases may flow;
   wherein the sheath is formed of a flexible material which can be stretched to conform to the shape of the instrument being protected such that the ribs of the inner surface of the sheath are maintained in frictional contact with the instrument.

3. The instrument tip protector of claim 2 further comprising a cap end on the sheath opposite to the open end.

4. The instrument tip protector according to claim 1, wherein at least one of the ribs terminates at the cap end.

5. The instrument tip protector of claim 2, wherein the sheath is formed of a flexible material which may be cut with a pair of scissors.

6. The instrument tip protector of claim 2, wherein the sheath is transparent.

7. The instrument tip protector of claim 2 further comprising a cap end on the sheath opposite to the open end, said cap end having an aperture.

8. The instrument tip protector according to claim 2, wherein said sheath is generally cylindrical.

9. A device for protecting a surgical instrument having a sharpened tip portion, comprising:
   an elastic sheath for covering at least the tip portion of said surgical instrument, said sheath being substantially solid to protect said instrument tip from damage; and
   a plurality of longitudinal ribs disposed on an inner surface of said sheath and adapted to contact the instrument for permitting gases to flow into said sheath in contact with the portions of said instrument covered by said sheath.

10. A surgical instrument tip protector comprising:
    a substantially solid, flexible sheath having an inner surface and an open end adapted to receive an instrument tip, said sheath being generally flat and arcuate; and
    a plurality of longitudinal ribs disposed on the inner surface of the sheath to provide spaces about an instrument tip covered by the sheath, through which fluid and gases may flow.

11. The device according to claim 10 further comprising an end cap disposed on one end of said sheath and having an aperture.

12. The device according to claim 11 wherein at least one of said longitudinal ribs terminates in said end cap.

13. A device for protecting a surgical instrument, comprising:
    a generally cylindrical, substantially solid, elastic sheath;
    an open end disposed on one end of said sheath;
    an end cap disposed on said sheath opposite said open end;
    an aperture disposed in said end cap; and
    at least one longitudinal rib disposed on an inner surface of said sheath extending from said open end to said end cap and adapted to contact the surface of a surgical instrument inserted into said sheath.

14. A surgical instrument tip protector comprising:
    a substantially solid, flexible sheath having an inner surface and an open end adapted to receive an instrument tip, said sheath formed of a material selected from the group consisting of PVC and polyurethane; and
    a plurality of longitudinal ribs disposed on the inner surface of the sheath to provide spaces about an instrument tip covered by the sheath, through which fluid and gases may flow.

* * * * *